(12) United States Patent
Yokhin et al.

(10) Patent No.: US 7,551,719 B2
(45) Date of Patent: *Jun. 23, 2009

(54) MULTIFUNCTION X-RAY ANALYSIS SYSTEM

(75) Inventors: Boris Yokhin, Nazareth Illit (IL); Alexander Krokhmal, Haifa (IL); Tzachi Rafaeli, Givat Shimshit (IL); Isaac Mazor, Haifa (IL); Amos Gvirtzman, Moshav Zippori (IL)

(73) Assignee: Jordan Valley Semiconductord Ltd, Migdal Ha'Emek (IL)

( * ) Notice: Subject to any disclaimer, the term of this patent is extended or adjusted under 35 U.S.C. 154(b) by 249 days.

This patent is subject to a terminal disclaimer.

(21) Appl. No.: 11/200,857

(22) Filed: Aug. 10, 2005

(65) Prior Publication Data
US 2006/0062351 A1   Mar. 23, 2006

Related U.S. Application Data

(63) Continuation-in-part of application No. 10/946,426, filed on Sep. 21, 2004, now Pat. No. 7,120,228.

(51) Int. Cl.
*G01B 15/02* (2006.01)
*G01N 23/20* (2006.01)
*G01N 23/201* (2006.01)

(52) U.S. Cl. .............. 378/90; 378/70; 378/86
(58) Field of Classification Search ............ 378/70–81, 378/86–90, 145–153, 114–116, 195–197, 378/210
See application file for complete search history.

(56) References Cited

U.S. PATENT DOCUMENTS 2,805,342 A  *  9/1957  Lang ..................... 378/71

(Continued)

FOREIGN PATENT DOCUMENTS

JP    05-188019    *  7/1993

(Continued)

OTHER PUBLICATIONS

Bowen et al., "X-Ray metrology by Diffraction and Reflectivity," *Characterization and Metrology for ULSI Technology: 2000 International Conference* (American Institute of Physics, 2001), pp. 570-579.

(Continued)

*Primary Examiner*—Edward J Glick
*Assistant Examiner*—Anastasia Midkiff
(74) *Attorney, Agent, or Firm*—Weingarte, Schurgin, Gagnebin & Lebovici LLP (57) ABSTRACT

Apparatus for analysis of a sample includes a radiation source, which is adapted to direct a first, converging beam of X-rays toward a surface of the sample and to direct a second, collimated beam of the X-rays toward the surface of the sample. A motion assembly moves the radiation source between a first source position, in which the X-rays are directed toward the surface of the sample at a grazing angle, and a second source position, in which the X-rays are directed toward the surface in a vicinity of a Bragg angle of the sample. A detector assembly senses the X-rays scattered from the sample as a function of angle while the radiation source is in either of the first and second source configurations and in either of the first and second source positions. A signal processor receives and processes output signals from the detector assembly so as to determine a characteristic of the sample.

36 Claims, 5 Drawing Sheets

U.S. PATENT DOCUMENTS

| | | | |
|---|---|---|---|
| 4,242,588 A * | 12/1980 | Silk et al. | 378/34 |
| 4,696,024 A * | 9/1987 | Pesch | 378/73 |
| 4,725,963 A | 2/1988 | Taylor et al. | |
| 4,847,882 A | 7/1989 | Knoth et al. | |
| 4,989,226 A | 1/1991 | Woodbury et al. | |
| 5,151,588 A | 9/1992 | Kiri et al. | |
| 5,373,544 A * | 12/1994 | Goebel | 378/71 |
| 5,574,284 A | 11/1996 | Farr | |
| 5,619,548 A | 4/1997 | Koppel | |
| 5,740,226 A | 4/1998 | Komiya et al. | |
| 5,850,425 A * | 12/1998 | Wilkins | 378/85 |
| 5,923,720 A | 7/1999 | Barton et al. | |
| 5,949,847 A | 9/1999 | Terada et al. | |
| 5,963,329 A | 10/1999 | Conrad et al. | |
| 6,041,098 A | 3/2000 | Touryanski et al. | |
| 6,192,103 B1 | 2/2001 | Wormington et al. | |
| 6,226,347 B1 | 5/2001 | Golenhofen | |
| 6,226,349 B1 | 5/2001 | Schuster et al. | |
| 6,381,303 B1 | 4/2002 | Vu et al. | |
| 6,389,102 B2 | 5/2002 | Mazor et al. | 378/89 |
| 6,453,006 B1 | 9/2002 | Koppel et al. | |
| 6,507,634 B1 | 1/2003 | Koppel et al. | |
| 6,512,814 B2 | 1/2003 | Yokhin et al. | |
| 6,556,652 B1 | 4/2003 | Mazor et al. | |
| 6,625,250 B2 * | 9/2003 | Houge | 378/84 |
| 6,639,968 B2 | 10/2003 | Yokhin et al. | |
| 6,643,354 B2 | 11/2003 | Koppel et al. | |
| 6,680,996 B2 | 1/2004 | Yokhin et al. | |
| 6,711,232 B1 | 3/2004 | Janik | |
| 6,744,950 B2 | 6/2004 | Aleksoff | |
| 6,750,952 B2 | 6/2004 | Grodnesnsky et al. | |
| 6,754,304 B1 | 6/2004 | Kumakhov | 378/45 |
| 6,754,305 B1 | 6/2004 | Rosencwaig et al. | |
| 6,771,735 B2 | 8/2004 | Janik et al. | |
| 6,810,105 B2 | 10/2004 | Nasser-Ghodsi et al. | 378/44 |
| 6,895,075 B2 | 5/2005 | Yokhin et al. | |
| 6,898,270 B2 * | 5/2005 | Lange et al. | 378/147 |
| 6,996,208 B2 * | 2/2006 | Helming et al. | 378/70 |
| 7,062,013 B2 * | 6/2006 | Berman et al. | 378/82 |
| 7,068,753 B2 * | 6/2006 | Berman et al. | 378/70 |
| 7,110,491 B2 | 9/2006 | Mazor et al. | |
| 7,120,228 B2 * | 10/2006 | Yokhin et al. | 378/90 |
| 7,158,608 B2 * | 1/2007 | Kucharczyk | 378/71 |
| 7,213,686 B2 * | 5/2007 | Kaufman | 187/262 |
| 7,242,745 B2 * | 7/2007 | He et al. | 378/81 |
| 2001/0028699 A1 | 10/2001 | Iwasaki | |
| 2001/0043668 A1 | 11/2001 | Hayashi et al. | |
| 2002/0097837 A1 | 7/2002 | Fanton et al. | |
| 2002/0110218 A1 | 8/2002 | Koppel et al. | |
| 2003/0043965 A1 * | 3/2003 | Bahr et al. | 378/70 |
| 2003/0157559 A1 | 8/2003 | Omote et al. | |
| 2004/0052330 A1 | 3/2004 | Koppel et al. | |
| 2004/0109531 A1 | 6/2004 | Yokhin et al. | |
| 2004/0131151 A1 | 7/2004 | Berman et al. | |
| 2004/0156474 A1 | 8/2004 | Yokhin et al. | |
| 2004/0218717 A1 | 11/2004 | Koppel et al. | |
| 2006/0023836 A1 | 2/2006 | Berman et al. | |
| 2006/0088139 A1 * | 4/2006 | Nakano et al. | 378/79 |
| 2006/0115046 A1 | 6/2006 | Berman et al. | |
| 2006/0182220 A1 | 8/2006 | Berman et al. | |

FOREIGN PATENT DOCUMENTS

| | | |
|---|---|---|
| JP | 07-311163 | 11/1995 |
| JP | 10-048398 | 2/1998 |
| JP | 11014561 | 1/1999 |
| WO | WO 01/24200 | 4/2001 |
| WO | WO 03087795 A2 * | 10/2003 |

OTHER PUBLICATIONS

Goorsky et al., "Grazing Incidence In-plane Diffraction Measurement of In-plane Mosaic with Microfocus X-ray Tubes," *Crystal Research and Technology* 37:7 (2002), pp. 645-653.

Parrill et al., "GISAXS—Glancing Incidence Small Angle X-ray Scattering," *Journal de Physique IV* 3 (Dec. 1993), pp. 411-417.

"Grazing incidence in-plane diffraction measurement of in-plane mosaic with microfocus X-ray tubes", By Goorsky, et al., Crystal Research and Technology 37:7 (2002), pp. 645-653.

Wiener et al., "Characterization of Titanium Nitride Layers by Grazing-Emission X-Ray Fluorescence Spectrometry," in Applied Surface Science 125 (1998), p. 129.

Hayashi et al., "Refracted X-Rays Propagating Near the Surface under Grazing Incidence Condition," Spectrochimica Acta, Part B 54, 1999, pp. 227-230.

Series 5000 Model XTF5011 X-Ray Tube Information, Oxford Instruments Inc., Scotts Valley, GA, U.S.A., Jun. 1998.

Monolithic Polycapillary Lens Information, X-Ray Optical Systems, Inc., Albany, NY, U.S.A., Dec. 29, 1998. (web site: www.xos.com).

S. Di Fonzo et al., "Non-Destructive Determination of Local Strain with 100-Nanometre Spatial Resolution," Nature, vol. 403, Feb. 10, 2000. (web site: www.nature.com).

Hugues Guerault, "Specular reflectivity and off-specular scattering," Tools for roughness investigation, Dec. 2000.

Jones, et al., "Small angle x-ray scattering for sub-100 nm pattern characterization," Applied Physics Letters 83:19 (2003), pp. 4059-4061.

Hu et al., "Small angle x-ray scattering metrology for sidewall angle and cross section of nanometer scale line gratings," Journal of Applied Physics 96:4 (2004), pp. 1983-1987.

Wu et al., "Small angle neutron scattering measurements of nanoscale lithographic features," Journal of Applied Physics 88:12 (2000), pp. 7298-7303.

Kojima, et al., "Structural characterization of thin films by x-ray reflectivity," Rigaku Journal 16:2 (1999), pp. 31-41.

Stommer, "X-ray scattering from silicon surfaces," in Semiconductor International (May 1, 1998).

Yoneda, "Anomalous surface reflection of X Rays," Physical Review 131, pp. 2010-2012, 1963.

Stommer, et al., "Characterization of semiconductor materials by X-ray scattering," Electrochemical Society Proceedings, vol. 99-16, pp. 117-133, 1999.

Ulyanekov, "Introduction to high resolution X-Ray diffraction," Workshop on X-ray characterization of thin layers (Uckley, May 21, 23, 2003).

Ito, "X-ray Scattering Method for Determining Pore-Size Distribution in Low-k Thin Films," Presented at the International Sematech Ultra-Low-k Workshop (San Francisco, CA, Jun. 6-7, 2002).

Naudon, et al., "New apparatus for grazing X-ray reflectometry in the angle-resoived dispersive mode," J. Appl. Cryst. 1989, vol. 22, pp. 46-464.

N. Wu, et al., "Substepping and its Application to HST Imaging," Jul. 28, 2003.

Wormington, Characterization of Pore Size Distribution in Low k Dielectrics Using X-ray Reflectivity, presented at the Sematech Gate Stack Engineering Workshop (Austin, Texas, May 2, 2002).

J. Spear, "Metrology for low-k materials," Silknet Alliance, 2003.

Jaklevic, et al, "High Rate X-Ray Fluorescence Analysis by Pulsed Excitation," IEEE Transactions on Nuclear Science NS-19:3 (1972), pp. 392-395.

Jaklevic, et al., "Small X-Ray Tubes for Energy Dispersive Analysis Using Semiconductor Spectrometers," Advances in X-Ray Alaysis 15 (1972) pp. 266-275.

Jaklevic, et al., "Energy Dispersive X-Ray Fluorescence Spetrometry Using Pulsed X-Ray Excitation," Advances in X-Ray Analysis 19 (1976).

Kozaczek, et al., "X-ray Diffraction Metrology for 200mm Process Qualification and Stability Assessment," Advanced Metallization Conference (Montreal, Canada) Oct. 8-11, 2001.

U.S. Appl. No. 11/389,490, Office Action dated May 1, 2008.

* cited by examiner

MULTIFUNCTION X-RAY ANALYSIS SYSTEM

CROSS-REFERENCE TO RELATED APPLICATION

This application is a continuation-in-part of U.S. patent application Ser. No. 10/946,426, filed Sep. 21, 2004, now U.S. Pat. No. 7,120,228 which is assigned to the assignee of the present patent application and whose disclosure is incorporated herein by reference.

FIELD OF THE INVENTION

The present invention relates generally to analytical instruments, and specifically to instruments and methods for material analysis using X-rays.

BACKGROUND OF THE INVENTION

X-ray reflectometry (XRR) is a well-known technique for measuring the thickness, density and surface quality of thin film layers deposited on a substrate. Such reflectometers typically operate by irradiating a sample with a beam of X-rays at grazing incidence, i.e., at a small angle relative to the surface of the sample, in the vicinity of the total external reflection angle of the sample material. Measurement of X-ray intensity reflected from the sample as a function of angle gives a pattern of interference fringes, which is analyzed to determine the properties of the film layers responsible for creating the fringe pattern. Exemplary systems and methods for XRR are described in U.S. Pat. Nos. 5,619,548, 5,923,720, 6,512,814, 6,639,968, and 6,771,735, whose disclosures are incorporated herein by reference.

Small-angle X-ray scattering (SAXS) is another method for surface layer characterization. It is described, for example, by Parrill et al., in "GISAXS—Glancing Incidence Small Angle X-ray Scattering," *Journal de Physique IV* 3 (December, 1993), pages 411-417, which is incorporated herein by reference. In this method, an incident X-ray beam is totally externally reflected from a surface. The evanescent wave within the surface region is scattered by microscopic structures within the region. Measurement of the scattered evanescent wave can provide information about these structures. For example, SAXS can be used in this manner to determine characteristics of pores in a surface layer of a low-k dielectric material formed on a silicon wafer.

U.S. Pat. No. 6,895,075, whose disclosure is incorporated herein by reference, describes methods and systems for performing combined XRR and SAXS measurements on a sample. Although XRR and SAXS are complementary in terms of the information they provide, there are difficulties inherent in performing both types of measurements using a single system. In terms of irradiation of the sample, for precise measurement of SAXS, a collimated beam is advantageous. On the other hand, XRR may advantageously use a converging beam with a large convergence angle, so that reflectivity measurements may be made over a range of several degrees simultaneously. In the embodiments disclosed in U.S. Pat. No. 6,895,075, X-ray inspection apparatus comprises a radiation source, which is configured to irradiate a small area on a surface of a sample. The X-ray optics control the radiation beam so as to adjust the angular width and height of the beam appropriately for XRR or SAXS.

On the detection side, SAXS typically looks at scattering as a function of azimuth, within the surface plane of the sample, while XRR is based on measuring reflected X-rays as a function of elevation, perpendicular to the surface plane. In the embodiments described in U.S. Pat. No. 6,895,075, the detection assembly comprises an array of detector elements, which is positioned to receive radiation that is reflected or scattered from the irradiated area. The array has two operative configurations: one in which the elements of the array resolve the radiation along an axis perpendicular to the plane of the sample, and another in which the elements resolve the radiation along an axis parallel to the plane. The appropriate configuration is selected, mechanically or electronically, for the type of measurement being performed.

X-ray diffractometry (XRD) is a well-known technique for studying the crystalline structure of matter. In XRD, a sample is irradiated by a monochromatic X-ray beam, and the locations and intensities of the diffraction peaks are measured. The characteristic scattering angles and the scattered intensity depend on the lattice planes of the sample under study and the atoms that occupy those planes. For a given wavelength $\lambda$ and lattice plane spacing d, diffraction peaks will be observed when the X-ray beam is incident on a lattice plane at angles $\theta$ that satisfy the Bragg condition: $n\lambda = 2d \sin \theta$, wherein n is the scattering order. The angle $\theta$ that satisfies the Bragg condition is known as the Bragg angle. Distortions in the lattice planes due to stress, solid solution, or other effects lead to observable changes in the XRD spectrum.

XRD has been used, inter alia, for measuring characteristics of crystalline layers produced on semiconductor wafers. For example, Bowen et al. describe a method for measuring germanium concentration in a SiGe structure using high-resolution XRD in "X-Ray metrology by Diffraction and Reflectivity," *Characterization and Metrology for ULSI Technology,* 2000 *International Conference* (American Institute of Physics, 2001), which is incorporated herein by reference.

XRD may also be used at grazing incidence to observe structures on the surface of a sample. For example, Goorsky et al. describe the use of grazing-incidence XRD for analyzing epitaxial layer structures on a semiconductor wafer in "Grazing Incidence In-plane Diffraction Measurement of In-plane Mosaic with Microfocus X-ray Tubes," *Crystal Research and Technology* 37:7 (2002), pages 645-653, which is incorporated herein by reference. The authors apply the technique to determine the in-plane lattice parameter and lattice orientation of very thin surface and buried semiconductor layers.

In the context of the present patent application and in the claims, the terms "scatter" and "scattering" are used to refer to any and all processes by which X-ray irradiation of a sample causes X-rays to be emitted from the sample. Thus, in this context, "scattering" includes the phenomena of XRR, XRD and SAXS, as well as other scattering phenomena known in the art, such as X-ray fluorescence (XRF). On the other hand, the specific term "small-angle X-ray scattering," abbreviated SAXS, refers to the particular phenomenon of grazing-incidence scattering in the sample plane, as described above.

SUMMARY OF THE INVENTION

The above-mentioned U.S. patent application Ser. No. 10/946,426 describes a system for rapid XRR- and XRD-based analysis of a sample. A radiation source directs a converging beam of the X-rays toward a surface of the sample, such as a semiconductor wafer. A detector array senses X-rays scattered from the sample as a function of elevation angle over a range of elevation angles simultaneously. The system has XRR and XRD configurations. In the XRR configuration, the radiation source and detector array are positioned so that the array senses X-rays that are reflected from the surface of the sample at grazing angles. In the XRD configuration, the radiation source and detector array are positioned so that the array senses X-rays that are diffracted from the surface in a vicinity of the Bragg angle of the sample. A motion assembly may be provided to shift the radiation source and detector array between the XRR and XRD configurations.

Some embodiments of the present invention take the combined system one step further, so that it also provides SAXS measurement capabilities. For this purpose, the X-ray optics associated with the radiation source are configurable to generate either a converging beam or a collimated beam. The converging beam is used for XRR and high-resolution XRD measurements, with the detector array arranged to resolve scattered radiation along an axis perpendicular to the plane of the sample. The collimated beam may be used to perform rapid, low-resolution XRD measurements, as well as for SAXS measurement. For the purpose of SAXS, the detector array is arranged to resolve scattered radiation along an axis parallel to the sample plane.

Additionally or alternatively, the system may be configurable to perform grazing-incidence XRD measurement, as well.

Thus, a single X-ray source may be used to perform multiple different (and complementary) X-ray scattering measurements on a given sample. These combined capabilities are useful particularly for X-ray metrology of thin films, in order to determine the density, thickness, crystalline structure, porosity, and other properties of thin film layers. Alternatively or additionally, the principles of the present invention may be applied in other fields of X-ray analysis and metrology. Further alternatively, aspects of the embodiments described hereinbelow may be used in systems that are dedicated to one type of scattering measurement, such as SAXS, without necessarily providing multi-function capabilities.

There is therefore provided, in accordance with an embodiment of the present invention, apparatus for analysis of a sample, including:

a radiation source, which is adapted to direct a first, converging beam of X-rays toward a surface of the sample and to direct a second, collimated beam of the X-rays toward the surface of the sample;

a motion assembly, which is operative to move the radiation source between a first source position, in which the X-rays are directed from the radiation source toward the surface of the sample at a grazing angle, and a second source position, in which the X-rays are directed from the radiation source toward the surface of the sample in a vicinity of a Bragg angle of the sample;

a detector assembly, which is arranged to sense the X-rays scattered from the sample as a function of angle while the radiation source is in either of the first and second source configurations and in either of the first and second source positions, and to generate output signals responsively to the scattered X-rays; and a signal processor, which is coupled to receive and process the output signals so as to determine a characteristic of the sample.

In disclosed embodiments, the radiation source includes an X-ray tube, which is operative to emit the X-rays; a first mirror, which is arranged to receive and focus the X-rays into the converging beam; and a second mirror, which is arranged to receive and focus the X-rays into the collimated beam. Typically, the first and second mirrors include doubly-curved structures.

In some embodiments, the motion assembly is operative to move the detector assembly between a first detector elevation, at which the detector assembly senses the X-rays scattered from the sample at the grazing angle, and a second detector elevation, at which the detector assembly senses the X-rays scattered from the surface in the vicinity of the Bragg angle. The motion assembly may also be operative to move the detector assembly at the first detector elevation between a first azimuth, at which the detector assembly senses small-angle scattering of the X-rays, and a second, higher azimuth, at which the detector assembly senses the X-rays that are diffracted from an in-plane structure on the surface of the sample.

In a disclosed embodiment, the detector assembly includes a detector array having a first detector configuration for resolving the scattered X-rays along a first axis perpendicular to the surface of the sample, and a second detector configuration for resolving the scattered X-rays along a second axis parallel to the surface. Typically, the signal processor is adapted to process the output signals from the detector assembly in the first detector configuration so as to determine a reflectance of the surface as a function of elevation angle relative to the surface, and to process the output signals from the detector assembly in the second detector configuration so as to determine a scattering profile of the surface as a function of azimuthal angle in a plane of the surface.

In some embodiments, the signal processor is adapted to process the output signals from the detector assembly while the radiation source emits the first beam and is in the first source position so as to acquire an X-ray reflectance (XRR) spectrum of the surface, and to process the output signals from the detector assembly while the radiation source emits the second beam and is in the first source position so as to acquire at least one of a small-angle X-ray scattering (SAXS) spectrum and a grazing-incidence X-ray diffraction (XRD) spectrum of the surface, and to process the output signals from the detector assembly while the radiation source is in the second source position so as to acquire a high-angle XRD spectrum of the surface.

In one embodiment, the signal processor is adapted to acquire a high-resolution XRD spectrum while the radiation source is in the second source position and emits the first beam and to acquire a low-resolution XRD spectrum while the radiation source is in the second source position and emits the second beam. Typically, the motion sensor is adapted to position the detector assembly at a first distance from the surface of the sample for acquisition of the high-resolution XRD spectrum and to position the detector assembly at a second distance from the surface, smaller than the first distance, for acquisition of the low-resolution XRD spectrum.

Additionally or alternatively, when the sample includes at least one surface layer, the signal processor may be arranged to analyze two or more of the XRR, SAXS and XRD spectra together in order to determine a property of the at least one surface layer. Typically, the property includes at least one of a thickness, a density, a surface quality, a porosity, and a crystalline structure.

In a disclosed embodiment, the apparatus includes a knife edge, which is arranged parallel to the surface of the sample and adjacent to the selected area so as to define a gap between the surface and the knife edge and to block a portion of the beam that does not pass through the gap. The apparatus may also include a beam block, which is arranged to block the X-rays that have passed through the gap and continued to propagate along the beam axis, without blocking the scattered X-rays in an angular range of interest.

There is also provided, in accordance with an embodiment of the present invention, apparatus for analysis of a sample, including:

a radiation source, which is operative to direct a collimated beam of X-rays along a beam axis toward a selected area of the sample at a grazing angle, whereby some of the X-rays are scattered from the area over a range of azimuthal angles;

a knife edge, which is arranged parallel to a surface of the sample and adjacent to the selected area so as to define a gap between the surface and the knife edge and to block a portion of the beam that does not pass through the gap;

a beam block, which is arranged to block the X-rays that have passed through the gap and continued to propagate along the beam axis, without blocking the scattered X-rays in at least a part of the range of azimuthal angles;

a detector assembly, which is arranged to sense the scattered X-rays as a function of the azimuthal angles and to generate output signals responsively to the scattered X-rays; and a signal processor, which is coupled to receive and process the output signals so as to determine a characteristic of the sample.

In a disclosed embodiment, the apparatus includes at least one slit, which is perpendicular to the surface of the sample and is positioned between the radiation source and the knife edge so as to pass at least a portion of the collimated beam while blocking scattered X-rays. The at least one slit may include a first slit positioned in proximity to the radiation source and a second slit positioned in proximity to the knife edge.

Additionally or alternatively, the detector assembly includes an array of detector elements having an array length, and an evacuable enclosure having a front side and a rear side separated by a distance that is at least equal to the array length, wherein the array is positioned at the rear side of the enclosure, and the enclosure includes a window at a front side thereof, which is adapted to allow the radiation to pass therethrough so as to impinge on the array.

There is additionally provided, in accordance with an embodiment of the present invention, apparatus for analysis of a sample, including:

a radiation source, which is operative to direct a beam of X-rays toward a selected area of the sample, whereby some of the X-rays are scattered from the area;

a knife edge, including a cylinder of X-ray absorbing material, which is arranged parallel to a surface of the sample and adjacent to the selected area so as to define a gap between the surface and the cylinder and to block a portion of the beam that does not pass through the gap;

a detector assembly, which is arranged to sense the scattered X-rays as a function of angle and to generate output signals responsively to the scattered X-rays; and a signal processor, which is coupled to receive and process the output signals so as to determine a characteristic of the sample.

In a disclosed embodiment, the cylinder of X-ray absorbing material includes a metal wire.

There is further provided, in accordance with an embodiment of the present invention, apparatus for analysis of a sample, including:

a mounting assembly, for receiving and adjusting an orientation of the sample during the analysis;

a radiation source, which is operative to direct a collimated beam of X-rays toward a selected area on a surface of the sample on the mounting assembly, whereby some of the X-rays are scattered from the area over a range of azimuthal angles;

a detector assembly, which is arranged to sense the scattered X-rays as a function of the azimuthal angles and to generate output signals responsively to the scattered X-rays; and a signal processor, which is adapted to receive a tilt map indicating a characteristic tilt angle of the surface, and to determine a tilt angle of the selected area based on the tilt map, and to direct the mounting assembly to adjust the orientation of the sample responsively to the estimated tilt angle, and which is coupled to receive and process the output signals after adjustment of the orientation so as to determine a characteristic of the sample.

Typically, the radiation source is adapted to direct a converging beam of the X-rays toward each of a plurality of locations on the surface, and the detector assembly is adapted to sense the X-rays reflected from the surface as a function of elevation angle relative to the surface, and the signal processor is adapted to measure an X-ray reflectance (XRR) spectrum of each of the locations responsively to the reflected X-rays and to determine the tilt angle at each of the locations based on the XRR spectrum.

There is moreover provided, in accordance with an embodiment of the present invention, a method for analysis of a sample, including:

operating a radiation source so as to direct a first, converging beam of X-rays toward a surface of the sample and to direct a second, collimated beam of the X-rays toward the surface of the sample;

moving the radiation source between a first source position, in which the X-rays are directed from the radiation source toward the surface of the sample at a grazing angle, and a second source position, in which the X-rays are directed from the radiation source toward the surface of the sample in a vicinity of a Bragg angle of the sample; and sensing the X-rays scattered from the sample as a function of angle while the radiation source is in both of the first and second source configurations and in both of the first and second source positions so as to determine a characteristic of the sample.

There is furthermore provided, in accordance with an embodiment of the present invention, a method for analysis of a sample, including:

directing a collimated beam of X-rays along a beam axis toward a selected area of the sample at a grazing angle, whereby some of the X-rays are scattered from the area over a range of azimuthal angles;

positioning a knife edge parallel to a surface of the sample and adjacent to the selected area so as to define a gap between the surface and the knife edge and to block a portion of the beam that does not pass through the gap;

positioning a beam block so as to block the X-rays that have passed through the gap and continued to propagate along the beam axis, without blocking the scattered X-rays in at least a part of the range of azimuthal angles; and sensing the scattered X-rays as a function of the azimuthal angles so as to determine a characteristic of the sample.

There is also provided, in accordance with an embodiment of the present invention, a method for analysis of a sample, including:

directing a beam of X-rays toward a selected area of the sample, whereby some of the X-rays are scattered from the area;

positioning a cylinder of X-ray absorbing material parallel to a surface of the sample and adjacent to the selected area so as to define a gap between the surface and the cylinder and to block a portion of the beam that does not pass through the gap; and sensing the scattered X-rays as a function of angle so as to determine a characteristic of the sample.

There is additionally provided, in accordance with an embodiment of the present invention, a method for analysis of a sample, including:

generating a tilt map of the sample;

directing a collimated beam of X-rays along a beam axis toward a selected area of the sample at a grazing angle, whereby some of the X-rays are scattered from the area over a range of azimuthal angles;

determining a tilt angle of the selected area based on the tilt map;

adjusting an orientation of the sample to compensate for the tilt angle; and sensing the scattered X-rays as a function of the azimuthal angles after adjusting the orientation, so as to determine a characteristic of the sample. The present invention will be more fully understood from the following detailed description of the embodiments thereof, taken together with the drawings in which:

DETAILED DESCRIPTION OF EMBODIMENTS

Figure 1:
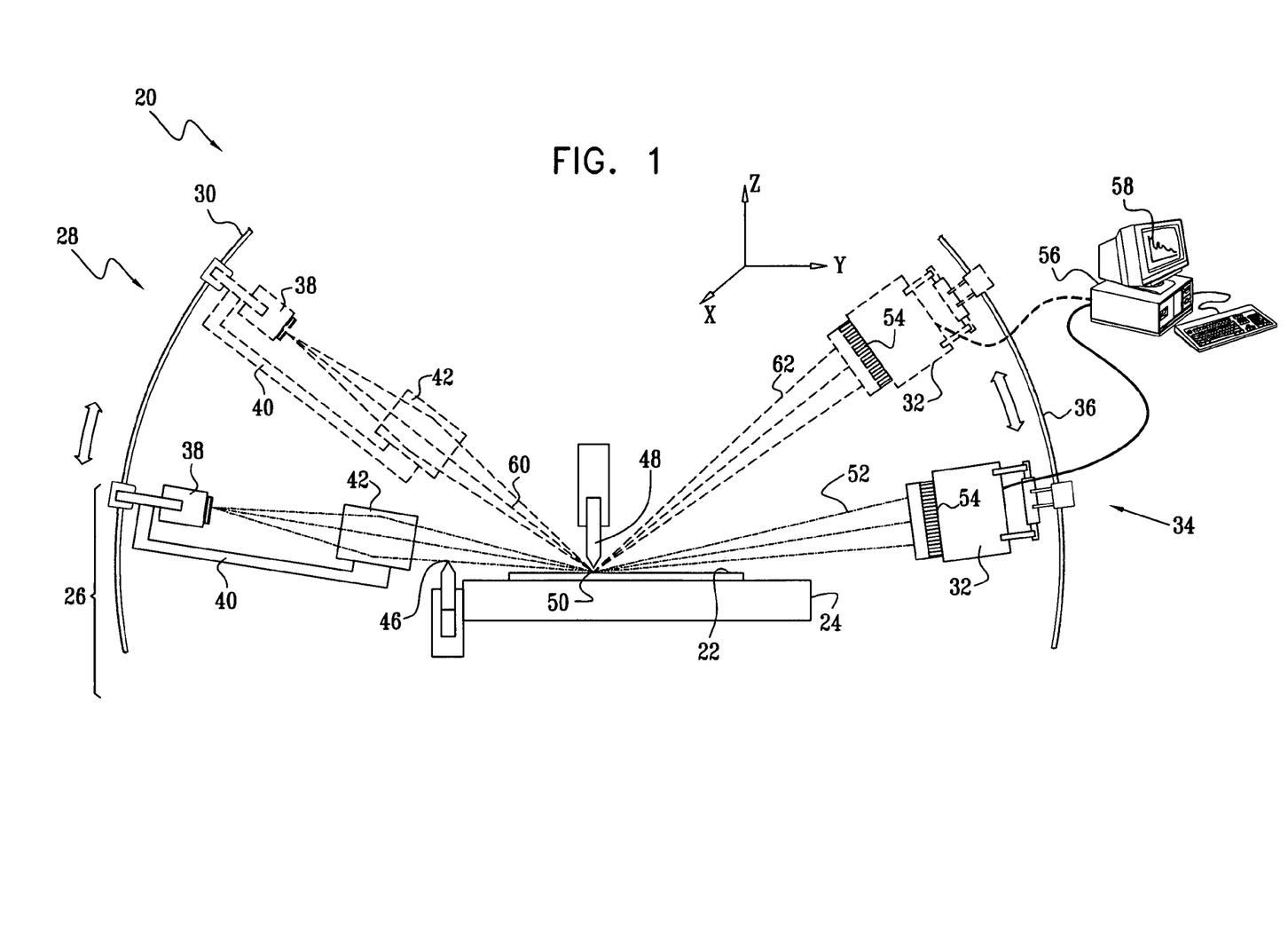
FIG. 1 is a schematic side view of an X-ray metrology system, in accordance with an embodiment of the present invention.

FIG. 1 is a schematic side view of a system 20 for measurement and analysis of X-ray scattering from a sample 22, in accordance with an embodiment of the present invention. System 20 is capable of performing X-ray reflectometry (XRR), small-angle X-ray scattering (SAXS) and X-ray diffractometry (XRD), in both high- and low-resolution modes. Sample 22 is mounted on a mounting assembly, such as a motion stage 24, allowing accurate adjustment of the position and orientation of the sample. An X-ray source 26 irradiates a small area 50 on sample 22. X-rays scattered from the sample are collected by a detector assembly 32.

A source motion assembly 28 shifts source 26 between upper and lower source positions for different types of measurements, as described hereinbelow. Similarly, a detector motion assembly 34 moves detector assembly 32 between upper and lower detector positions. The lower positions of the source and detector assemblies are typically used for XRR, SAXS, and optionally grazing-incidence XRD (GIXRD), whereas the upper positions are used for high-angle XRD, as described further hereinbelow. For GIXRD, the detector assembly is also shifted transversely, as described hereinbelow and shown in FIG. 2.

In the example shown in FIG. 1, the motion assemblies comprise curved tracks 30 and 36, along which source assembly 26 and detector assembly 32 are respectively translated, while maintaining the source and detector assembly at a constant distance from area 50. Alternatively or additionally, detector motion assembly 34 may be capable of changing the distance between the detector assembly and area 50, thereby changing the effective capture angle and angular resolution of detection. The source motion assembly may also be capable of this sort of axial motion (i.e., motion along the axis of the X-ray beam, in addition to the transverse vertical motion provided by tracks 30 and 36). Further additionally or alternatively, the detector motion assembly may be capable of rotating the detector assembly and/or shifting the detector assembly in the transverse horizontal direction, as described hereinbelow.

Curved tracks 30 and 36 are just one example of motion assemblies that may be used in system 20, and other suitable types of motion assemblies for these purposes will be apparent to those skilled in the art. For instance, the X-ray source and detector assembly may be mounted on respective plates, which may be tilted, raised and lowered to assume the positions shown in FIG. 1. All such types of motion assemblies are considered to be within the scope of the present invention. When the term "motion assembly" is used in the current patent application and in the claims without further elaboration, it should be taken to refer to either or both of the source and detector motion assemblies, depending on the context in which the term is used.

Alternatively, multiple X-ray sources and/or multiple detector assemblies may be used for the XRR and XRD measurements. In this case, the motion assemblies may not be needed. Further alternatively, a single X-ray tube may be shifted between lower and upper positions, while each position has its own stationary optics.

Figure 2:
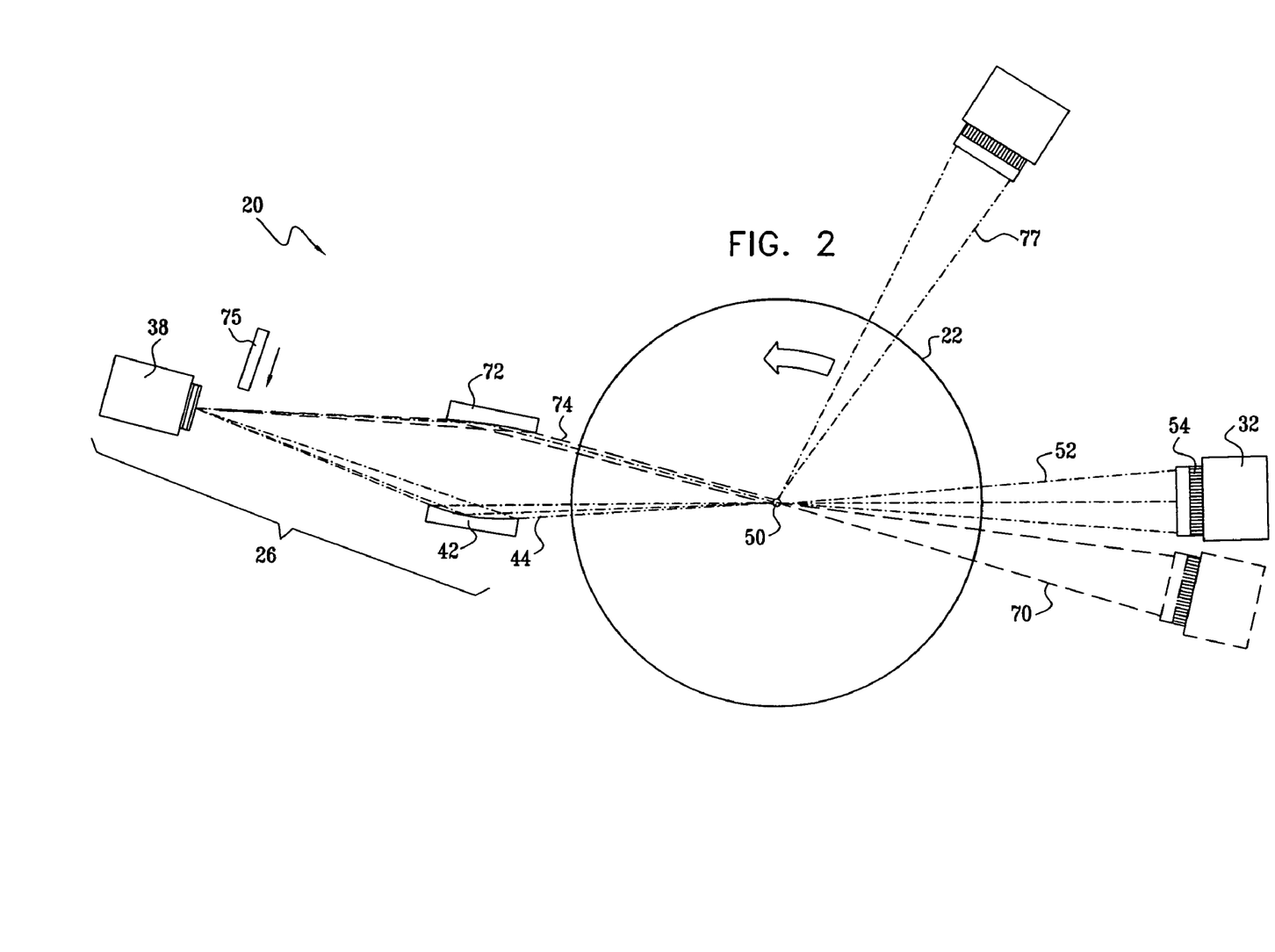
FIG. 2 is a schematic top view of an X-ray metrology system, in accordance with an embodiment of the present invention.

X-ray source 26 may be configured to produce either a converging X-ray beam or a collimated beam, as described in detail hereinbelow with reference to FIG. 3. FIG. 1 shows the converging-beam configuration used for XRR and high-resolution XRD measurements, while FIG. 2 shows both the converging beam and the collimated-beam configuration that is used for SAXS, GIXRD and conventional XRD measurements (referred to herein as "low-resolution" XRD, in distinction to the high-resolution XRD mode using a collimated beam). In the context of the present patent application and in the claims, a beam is considered to be "collimated" if its divergence (full angular width at half maximum power —FWHM) is less than 0.5°. This degree of collimation is sufficient for the types of SAXS and low-resolution XRD measurements that are made in system 20, although better collimation (for example, divergence of 0.3°) generally gives better results.

The table below summarizes the alternative configurations of system 20:

TABLE I

CONFIGURATION OPTIONS

| System measurement configuration | Source and detector positions | Incident beam configuration |
|---|---|---|
| XRR | Low angle | Converging |
| High-res XRD | High angle | Converging |
| SAXS | Low angle | Collimated |
| Low-res XRD | High angle | Collimated |
| GIXRD | Low angle | Collimated |

Turning now to the details of system 20, X-ray source 26 typically comprises an X-ray tube 38, which is mounted on a source mounting assembly 40. Tube 38 typically has a small emission area, to permit accurate focusing on the surface of sample 22. For example, tube 28 may comprise the XTF5011 X-ray tube, produced by Oxford Instruments (Scotts Valley, Calif.). A typical X-ray energy for reflectometric and scattering measurements in system 20 is about 8.05 keV (CuKα1). Alternatively, other energies may be used, such as 5.4 keV (CrKα1).

In the XRR configuration shown in FIG. 1, a focusing optic 42 focuses the beam emitted by tube 38 to a converging beam 44, which converges to a focus in area 50. Typically, optic 42 comprises a doubly-curved crystal, which also monochromatizes beam 44. Optics that may be used in system 20 for this purpose are described, for example, in U.S. Pat. No. 6,381,303. The optics may comprise a curved crystal monochromator, such as the Doubly-Bent Focusing Crystal Optic, produced by XOS Inc., of Albany, N.Y. Other suitable optics are described in the above-mentioned U.S. Pat. Nos. 5,619,548 and 5,923,720. The doubly-curved focusing crystal causes beam 44 to converge in both the horizontal and vertical directions, so as to focus approximately to a point in area 50. Alternatively, a cylindrical optic may be used to focus beam 34 so that the beam converges to a line on the sample surface. Further possible optical configurations will be apparent to those skilled in the art.

For XRR measurement, converging beam 44 strikes area 50 at a grazing angle, typically over a range of incident angles from about 0° to 4.5°, although larger or smaller ranges may be used. In this configuration, detector assembly 32 collects a diverging beam 52 of reflected X-rays over a range of angles in the vertical direction, as a function of elevation angle ($\phi$) between about 0° and at least 2°, and typically up to 3°. This range includes angles both below and above the critical angle of the sample for total external reflection, $\Phi_C$. (For clarity of illustration, the angular ranges shown in the figures are exaggerated, as is the elevation of source 26 and detector assembly 38 above the plane of sample 22 in the XRR configuration. For convenience and clarity in this figure and in the description that follows, the sample plane is arbitrarily taken to be the X-Y plane, wherein the Y-axis is parallel to the projection of the axis of the X-ray beam on the sample surface. The Z-axis is in the vertical direction, perpendicular to the sample plane.)

A dynamic knife edge 48 and shutter 46 may be used to limit the angular extent of incident beam 44 of the X-rays in the vertical direction (i.e., perpendicular to the plane of sample 22). The use of these beam-limiting optics in the XRR configuration is described in the above-mentioned U.S. Pat. No. 6,512,814. Knife edge 48 is also used, together with a beam block and beam-limiting slits (shown in FIG. 4, but omitted from FIG. 1 for simplicity), in order to reduce background scattering in the SAXS configuration. The heights of the knife edge and shutter relative to the sample surface are adjustable depending on the type of measurement being made and the range of measurement angles of interest.

Detector assembly 32 comprises a detector array 54, such as a CCD array. Although for simplicity of illustration, only a single row of detectors elements is shown in the figures, with a relatively small number of detector elements, array 54 generally includes a greater number of elements, arranged as either a linear array or a matrix (two-dimensional) array. Further aspects of detector assembly 32 and array 54 are described hereinbelow with reference to FIG. 4.

A signal processor 56 receives and analyzes the output of detector assembly 32, so as to determine a distribution 58 of the flux of X-ray photons scattered from sample 22 as a function of angle at a given energy or over a range of energies. Typically, sample 22 has one or more thin surface layers, such as thin films, at area 50, and distribution 58 as a function of angle exhibits a structure that is characteristic of interference, diffraction and/or other scattering effects due to the surface layer and interfaces between the layers. Processor 56 analyzes characteristics of the angular distribution in order to determine characteristics of one or more of the surface layers of the sample, such as the thickness, density, porosity, composition and surface quality of the layer, using methods of analysis described in the above-mentioned patents and patent application. Processor 56 (or another computer) may also serve as a system controller, to set and adjust the positions and configurations of the other system components.

The high-resolution XRD configuration of system 20 is useful particularly for assessing properties of monocrystalline films on sample 22. In this configuration, as noted in the table above, both source 26 and detector assembly 32 are shifted to relatively high angles, near the Bragg angle of sample 22. Source 26 irradiates area 50 with a converging beam 60 in the vicinity of the Bragg angle, and detector assembly 32 receives a diverging beam 62 over a range of angles in the vicinity of the Bragg angle. For the sake of this example, it is assumed that the lattice plane creating the diffraction pattern is roughly parallel to the surface of sample 22, so that the incidence and takeoff angles defined by beams 60 and 62 relative to the surface are both equal to the Bragg angle. This assumption is often true with respect to semiconductor substrates, such as silicon wafers, and monocrystalline thin film layers that are grown on such substrates. Alternatively, source 26 and detector assembly 32 may be positioned at different incidence and takeoff angles in order to measure diffraction from lattice planes that are not parallel to the surface of sample 22.

FIG. 2 is a schematic top view of system 20, in accordance with an embodiment of the present invention. This view shows X-rays from tube 38 striking both focusing optic 42 and a collimating optic 72 (which was omitted from FIG. 1 for clarity of illustration). Source mounting assembly 40 positions tube 38 so that the beam from the tube strikes optic 42 at the proper angle to make beam 44 converge onto area 50. The beam from X-ray tube 38 also strikes collimating optic 72 at a suitable angle to generate a collimated beam 74, which similarly impinges on area 50. Optic 72 may comprise, for example, a doubly-curved mirror with a multiplayer coating, which reflects radiation at 8 keV to create a beam with divergence <0.3° and spot size <100 μm. Optics of this sort are available from various manufacturers, such as Applied X-ray Optics (AXO, Dresden, Germany). This optic also monochromatizes the X-ray beam. For the types of focusing and collimating optics described hereinabove, the X-ray tube and optics are typically positioned so that the X-rays from the tube impinge on optic 42 at an angle of about 14° and on optic 72 at an angle of approximately 1°.

As a result of the optical arrangement of X-ray tube 38 and optics 42 and 72, converging beam 44 and collimated beam 74 are offset in azimuth, i.e., the beam axes are not collinear. The beam generated by X-ray tube 38 and the apertures of optics 42 and 72 may be wide enough so that the beam strikes both of optics 42 and 72 simultaneously, without moving the tube or optics. Alternatively, if a narrower beam and/or narrower apertures are used, the X-ray tube may be translated vertically between XRR and SAXS positions. In any case, only one of beams 44 and 74 is typically used in measurements at any given time. Therefore, a movable source beam block 75 may be deployed to block part of the beam from the X-ray tube so that only one of beams 44 and 74 strikes sample 22. (Alternatively, for some applications, the two beams may be generated simultaneously.) Because of the azimuthal offset, diverging beam 52 that is generated in XRR mode is offset in the X-direction from a scattered beam 70 that is generated in SAXS mode. In order to compensate for this offset, detector assembly 32 may be shifted in the X-direction depending on the operational mode of system 20. Alternatively, the detector assembly may comprise two detector arrays, which are positioned and oriented to capture beams 52 and 70, respectively.

With the source and detector assemblies in their high-angle positions, and the source assembly in the collimated-beam configuration, system 20 is well suited for low-resolution XRD measurement. This sort of measurement is useful, inter alia, in assessing phases and textures of polycrystalline structures, such as polycrystals in metal films on semiconductor wafers. Because of the uncontrolled orientation of these crystals, the XRD pattern they create is characterized by Debye rings. This phenomenon is described, for example, by Kozaczek et al., in "X-ray Diffraction Metrology for 200 mm Process Qualification and Stability Assessment," *Advanced Metallization Conference* (Montreal, Canada, Oct. 8-11, 2001), which is incorporated herein by reference.

The angular range over which the XRD pattern extends in this case is typically on the order of 10-20°. To cover this range, it may be desirable to advance detector assembly 32 closer to area 50 on sample 22, so that detector array 54 covers a relatively larger range than in the high-resolution configuration. Moving the array closer to the sample also degrades the angular resolution, but a resolution of about 0.3° is sufficient to differentiate between polycrystal phases. It is desirable for this purpose that optic 72 be chosen and adjusted so that beam 74 has a divergence that is no greater than about 0.3°.

For SAXS, source assembly 26 and detector assembly 32 are arranged in their lower positions. Optionally, for SAXS, source motion assembly 28 is operated to lower source assembly 26 slightly closer to the X-Y plane than for XRR, so that collimated beam 74 impinges on area 50 at a suitably low grazing angle. Alternatively, optic 72 may be held by assembly 40 at a lower elevation than optic 42, so that beam 74 is emitted from assembly 26 along a lower beam axis than beam 44. The orientation of detector array 54 may be rotated for SAXS, as described below, in order to collect and resolve scattered X-rays over a range of angles in the horizontal (azimuth-θ) direction. Typically, the scattering spectrum is measured over a range between about 0° and 3°. To enhance the angular resolution in SAXS, detector assembly 32 is typically held relative far from area 50.

For GIXRD, source assembly 26 is positioned roughly as it is for SAXS. Detector assembly 32, however, is typically shifted transversely by the detector motion assembly, in the plane of sample 22, to a higher azimuth in order to capture a diffracted beam 77. The azimuthal angle of diffracted beam 77 relative to the incident collimated beam 74 is determined by the Bragg angle of the in-plane structures on the sample surface that are responsible for the diffraction. Stage 24 (FIG. 1) may be configured to rotate sample 22 in the X-Y plane so as to align the in-plane lattice relative to the incident beam angle.

Figure 3A:
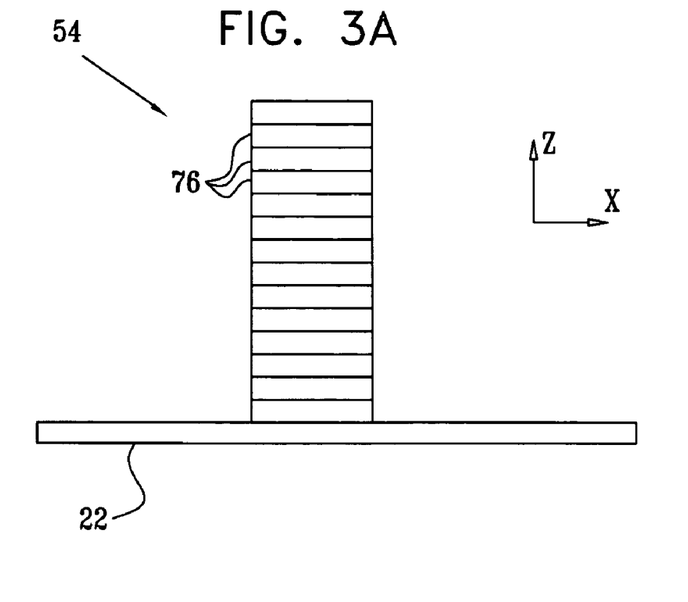
FIGS. 3A and 3B are schematic, frontal views of a detector array, configured for XRR and SAXS, respectively, in accordance with an embodiment of the present invention.
Figure 3B:
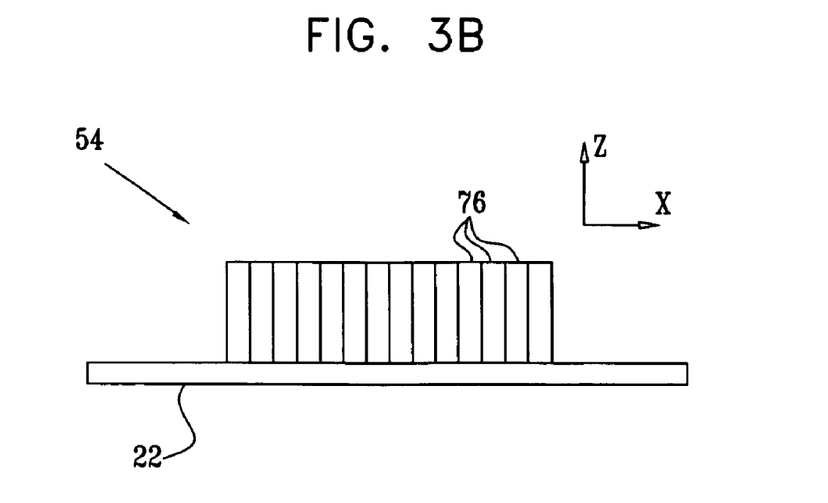

FIGS. 3A and 3B are schematic frontal views of detector array 54 in first and second operative configurations, respectively, in accordance with an embodiment of the present invention. The first configuration, shown in FIG. 3A, is used for XRR and high-angle XRD, whereas the second configuration, shown in FIG. 3B, is used for SAXS and GIXRD measurements. Array 54 is shown in these figures as comprising a single row of detector elements 76, with an array axis that can be aligned to resolve the incident radiation along either of two axes: the Z-axis, perpendicular to the plane of sample 22, for XRR and high-angle XRD, or the X-axis, parallel to the sample plane, for SAXS and GIXRD.

Detector elements 76 have a high aspect ratio, i.e., their width, in the direction transverse to the array axis, is substantially greater than their pitch along the axis. The high aspect ratio is useful in enhancing the signal/noise ratio of system 20, since array 54 is thus able to collect X-ray photons over a relatively wide area for each angular increment along the array axis. The dimensions of elements 76 are shown in the figures solely by way of example, however, and the principles of the present invention may be applied using elements of smaller or larger aspect ratio, depending on application needs and availability of suitable detector devices.

Detector array 54 may comprise either a linear array or a matrix array. In the latter case, the array may be operated in a line-binning mode, so that multiple detector elements in each row of the array function effectively as a single element with high aspect ratio. In this case, although array 54 physically comprises a two-dimensional matrix of detector elements, functionally the array takes the form of a single line of detector elements, depending on the direction of binning, as shown in FIGS. 4A and 4B. Alternatively, array 54 may comprise an array of PIN diodes with suitable readout circuits, possibly including integrated processing electronics, as described in U.S. Pat. No. 6,389,102. Further details regarding types of detector arrays that may be used in system 20 and adaptation of such arrays for use in XRR and SAXS are provided in the above-mentioned U.S. Pat. No. 6,895,075.

Detector motion assembly 34 may be configured to rotate detector assembly 32 mechanically between the orientations of FIGS. 3A and 3B. Alternatively, detector assembly 32 may itself comprise an array motion device (not shown) for rotating detector array 54 between the orientations of FIGS. 3A and 3B. Such hardware in either case rotates the array by 90° between the vertical and horizontal axes, depending on the type of measurement being made. If the point of rotation is near the center of array 54, then it may also be necessary to shift the array downward (closer to the plane of sample 22) for SAXS measurement, and upward for XRR. Alternatively, the point of rotation may be fixed near the plane of the sample, so that no vertical movement of the array is needed. Typically, in the SAXS configuration, array 54 is not centered about the axis of incident beam 74. Since SAXS is generally symmetrical about the incident beam axis, substantially no information is lost, and the angular range of the scattering measurement may be increased by positioning array 54 to measure the scattered radiation on one side of the axis, rather than both.

Figure 4:
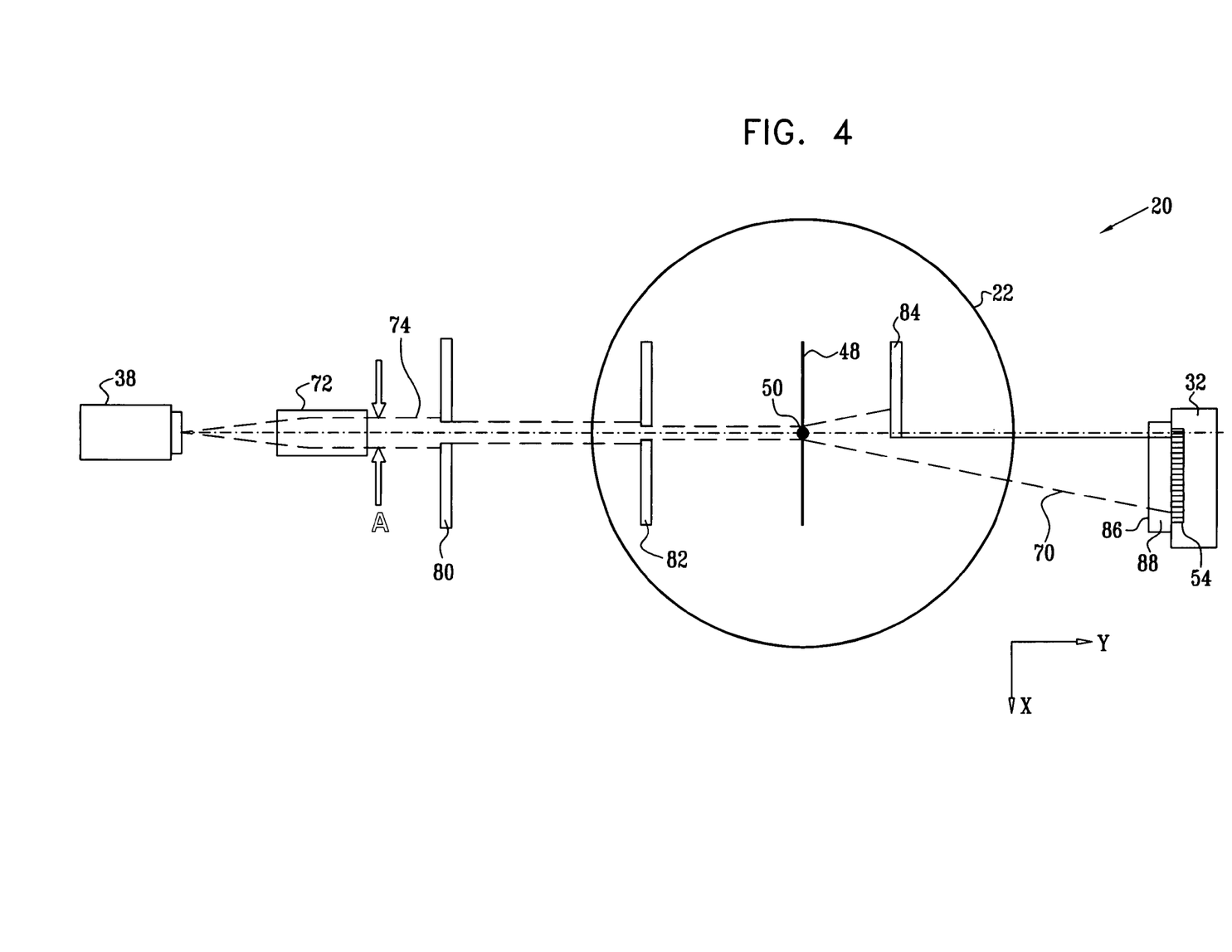
FIG. 4 is a schematic top view of a system for SAXS measurement, in accordance with an embodiment of the present invention.

FIG. 4 is a schematic top view of system 20, showing further details of the system configuration used in SAXS measurement, in accordance with an embodiment of the present invention. Because SAXS signals are generally weak, system 20 uses novel beam-control optics in order to reduce background scattering that may cause spurious X-rays to strike detector array 54 and thus mask the actual SAXS signal. Specifically, as shown in this figure, the system comprises an anti-scattering slit 80 and an anti-diffraction slit 82, as well as knife edge 48 and a beam block 84. The purpose of each of these components will now be explained.

Collimating optic 72 has an output aperture, marked "A" in FIG. 4, from which X-rays may diffract and/or scatter toward detector array 54. (In the case of the Xenocs mirror mentioned above, for example, the output aperture is 1.2×1.2 mm, and the collimated output beam has a divergence of approximately 0.3°. The center of aperture A is a small distance above the sample plane, typically about 1 mm or less.) Slit 82 blocks radiation that is scattered from the aperture from striking either detector array 54 directly or from striking sample 22 and reflecting toward the detector array. In an exemplary embodiment, slit 82 is approximately 0.4 mm wide and is positioned above sample 22 a short distance (typically <20 mm) in front of knife edge 48. For best results, the bottom of slit 82 is positioned as close as possible to the surface of the sample, typically less than about 80 µm above the surface.

Slit 80 is typically positioned close to the output aperture of optic 72 and blocks X-rays that are diffracted from this aperture. In an exemplary embodiment, slit 80 is about 1 mm wide and is located less than about 10 mm from aperture A, which itself is roughly 160 mm from focal area 50. Slit 80 typically extends both above and below the plane of sample 22.

Knife edge 48 is also positioned a small distance above sample 22. The knife edge blocks radiation that was scattered from the aperture of optic 72 and not intercepted by slit 82, as well as radiation scattered from slits 80 and 82 themselves or scattered from air molecules between optic 72 and area 50. One possible configuration of the knife edge is described below with reference to FIG. 5.

Properly collimated X-rays from optic 72 pass through slits 80 and 82 and beneath knife edge 48 and strike area 50 on sample 22. Most of the incident X-rays are either specularly reflected from the sample, along the Y-axis, or else pass directly beneath knife edge 48 without reflection. These X-rays may then scatter from air molecules and, as a consequence, strike detector array 54 at various angles. In order to reduce this undesired scattering, beam block 84 is positioned close behind knife edge 48 and a small distance above sample 22. In an exemplary embodiment, the beam block is about 30 mm behind the knife edge and less than 70 µm above the surface of the sample. The beam block is typically positioned off-center, as shown in the figure, and extends a small distance (for example, about 250 µm) across the beam axis in order to block the direct and specularly-reflected beams. As a result, detector array 54 receives substantially the entire flux of X-rays that are scattered from area 50 horizontally away from the Y-axis, while most of the parasitic scattering from air molecules is blocked.

For further protection against parasitic scattering, detector assembly 32 may comprise a window 86 made of a suitable X-ray transparent material, such as beryllium, spaced in front of detector array 54. The window defines an evacuable enclosure 88 adjacent to detector array 54. Typically, the distance from array 54 to window 86 is at least equal to the length of the array (as measured along the array axis, i.e., the X-direction in FIG. 3B), and may be two to three times the length of the array or even greater. The enclosure is evacuated during operation. Removal of the air from the region immediately in front of the detector array, along with distancing the window from the array, is useful in further reducing parasitic scattering of X-rays in the vicinity of the array. Further details of this sort of window structure are described in the above-mentioned U.S. Pat. No. 6,512,814.

Figure 5:
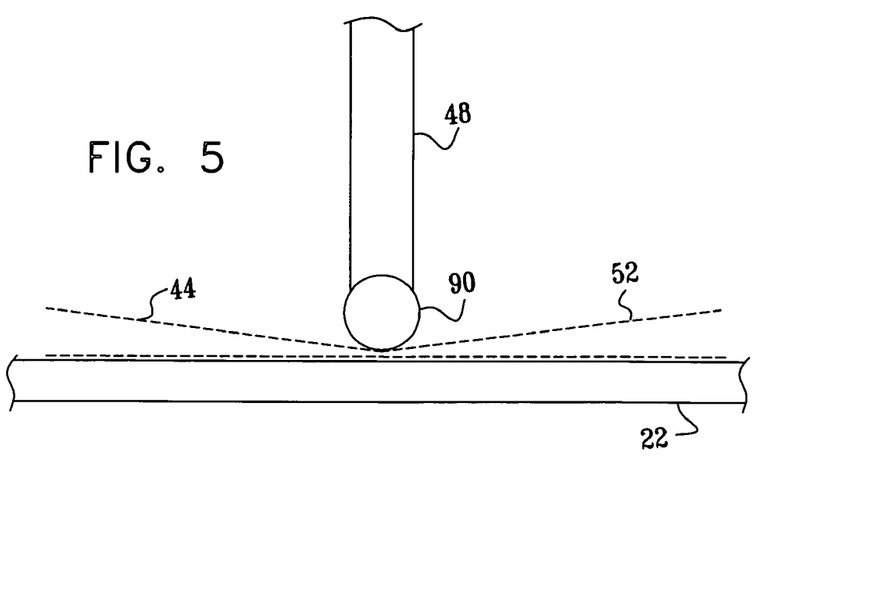
FIG. 5 is a schematic, detail view of a knife edge used to control the focus of an X-ray beam that is incident on a surface, in accordance with an embodiment of the present invention.

FIG. 5 is a schematic detail view of knife edge 48, in accordance with an embodiment of the present invention. In this embodiment, the lower edge of the knife, adjacent to the surface of sample 22, is made of a cylindrical, X-ray absorbing material, such as a metal wire 90. For example, for an X-ray beam with photon energy of 8 keV, wire 90 may comprise a piece of tantalum wire 200 µm in diameter. This arrangement permits the lower edge of the knife to be placed very close to the surface of the sample, on the order of 3 µm above the surface, without fear of damaging the sample.

Wire 90 can be aligned with the surface accurately and thus provides a small gap above the surface whose effective height is uniform over the entire angular range of interest, typically 0-4°. The alignment is invariant under rotation of the wire about its axis, in contrast to the situation when a flat-edged knife is used. Generally speaking, the size and uniformity of the gap between the knife edge and the surface define the size and uniformity of the X-ray focus on the surface. A small, uniform gap of the kind provided by wire 90 thus enhances the spatial resolution and angular accuracy of scattering measurements made in system 20. Based on this embodiment, it will be understood that in the context of the present patent application and in the claims, the term "knife edge" refers to any type of straight edge (not necessarily very sharp) that is positioned near the surface of the sample in order to create this sort of gap and block X-rays outside the gap.

Figure 6:
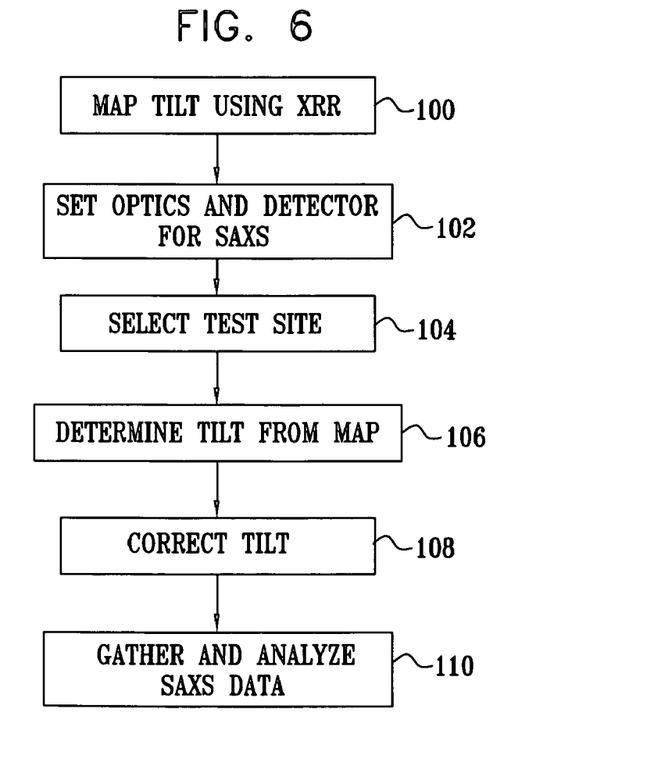
FIG. 6 is a flow chart that schematically illustrates a method for SAXS measurement, in accordance with an embodiment of the present invention.

FIG. 6 is a flow chart that schematically illustrates a method for performing SAXS measurements in system 20, in accordance with an embodiment of the present invention. The intensity of the SAXS signal is strongly dependent on the average incidence angle of beam 74 (FIG. 4) on the surface of area 50. The incidence angle, in turn, is directly affected by sample tilt. In a typical SAXS application, beam 74 is aimed to impinge on the surface of the sample at around 0.4°. If SAXS measurements are made at different points on the surface of sample 22, and the tilt varies by ±0.1°, for instance, the incidence angle will vary over the surface between 0.3° and 0.5°. These angle variations will cause large, spurious variations in the intensity of the SAXS spectra that are measured at the different points.

For example, in a typical application of system 20, sample 22 is a semiconductor wafer, which is held in place on stage 24 by suction exerted through vacuum ports (not shown) in the surface of the stage. Under these circumstances, the wafer conforms to the shape of the stage, with deformations due to the force of the suction. As a result, the local tilt angle of the wafer may vary from point to point on the wafer surface.

The method of FIG. 6 provides a solution to the problem of sample tilt in SAXS by using the XRR measurement capabilities of system 20. For this purpose, system 20 is operated in XRR mode to map the tilt of sample 22, at a tilt mapping step 100. An exemplary method of tilt mapping that may be used for this purpose is described in U.S. patent application Ser. No. 11/000,044, which is assigned to the assignee of the present patent application. To produce the map, the surface of the sample is divided into regions, and the surface tilt is measured in each region to give a tilt value. (The map may be produced using the SAXS sample itself, or using a reference sample, such as a bare silicon wafer.) Any suitable method may be used to determine the surface tilt. Exemplary methods for measuring tilt using XRR are described in U.S. Patent Application Publications US 2004/0109531 A1 and US 2004/0131151 A1, as well as in the above-mentioned U.S. Pat. No. 6,895,075. Additionally or alternatively, optical methods may be used for tilt measurement, as described, for example, in U.S. Pat. No. 6,643,354. The tilt map is stored by the system controller (a role that may be filled by processor 56, as noted above).

After the tilt map has been produced, source assembly 26 and detector assembly 32 are set for SAXS measurement, as described above, at a mode setting step 102. Stage 24 is then operated to move sample 22 so that X-ray beam 74 impinges on a desired test site, at a site selection step 104. Typically, multiple sites on sample 22 are preselected for this purpose, and stage 24 moves the sample so that each site in turn is located in area 50. The system controller looks up the stored tilt value for this site on the tilt map, at a tilt determination step 106. Alternatively, if there is no stored tilt value for this precise site, the system controller may look up the tilt values of neighboring points on the tilt map and find the approximate tilt value of the test site by interpolation. If the XRR and SAXS beam axes are mutually offset, as shown in FIG. 2, a rotation transformation may also be applied to the tilt values to account for the angular offset in the X-Y plane.

The system controller then instructs stage 24 to adjust the orientation angle of sample 22 in order to compensate for the tilt at the current test site, at a tilt correction step 108. In other words, if it has been determined from the tilt map that the current test site is tilted +0.1° about the X-axis, stage 24 will apply a tilt of −0.1°. Alternatively, the X-ray beam axis of source assembly 26 may be adjusted in order to compensate for the sample tilt. Once the tilt has been properly adjusted, the source and detector assemblies are actuated, and processor 56 collects and analyzes the SAXS spectrum of the test site, at a data collection step 110. This process is then repeated at the remaining test sites.

Although the embodiments described above deal mainly with determining surface layer characteristics of semiconductor wafers, the principles of the present invention can similarly be used in other applications of X-ray-based analysis, as well as in other types of radiation-based analysis, using not only X-rays, but also other ionizing radiation bands. Furthermore, system 20 may be modified to incorporate other methods of radiation-based analysis, such as X-ray fluorescence measurement, as described, for example, in U.S. Pat. No. 6,381,303. Alternatively or additionally, system 20 may be configured to perform diffuse XRR measurements, as described in U.S. patent application Ser. No. 10/902,177, filed Jul. 30, 2004, which is assigned to the assignee of the present patent application.

Furthermore, although features of the present invention are described hereinabove with reference to system 20, which combines multiple different modes of X-ray analysis, some of these features may alternatively be implemented in systems that provide only one or two operating modes, such as SAXS, XRD (high angle or grazing incidence) and/or XRR.

The principles of the present invention may also be applied in measuring systems and tools for use in production environments. For example, in an alternative embodiment of the present invention (not shown in the figures), elements of system 20 are integrated with a semiconductor wafer fabrication tool to provide in situ inspection. Typically, the fabrication tool comprises a vacuum chamber containing deposition apparatus for creating thin films on a wafer, as is known in the art. The chamber has X-ray windows, as described, for instance, in U.S. Patent Application Publication US 2001/0043668 A1. X-ray source assembly 26 may then irradiate area 50 on the wafer via one of windows, and detector assembly 32 receives the scattered X-rays through another window, in one or more of the XRR, XRD or SAXS configurations, as described above. In another alternative embodiment, system 20 may be configured as a station in a cluster tool, along with other stations used in performing production steps.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus for analyzing a sample, the apparatus comprising:
 a radiation source, which is adapted to direct a first, converging beam of X-rays toward a surface of the sample and to direct a second, collimated beam of the X-rays toward the surface of the sample, and which comprises:
  an X-ray tube, which is operative to emit the X-rays;
  a first mirror, which is arranged to receive and focus the X-rays into the converging beam; and
  a second mirror, which is arranged to receive and focus the X-rays into the collimated beam;
 a detector assembly, which is arranged to sense the X-rays scattered from the sample as a function of angle responsively to either of the converging beam and the collimated beam, and to generate output signals responsively to the scattered X-rays; and
 a signal processor, which is coupled to receive and process the output signals so as to determine a characteristic of the sample.

2. The apparatus according to claim 1, further comprising a motion assembly, which is operative to move the radiation source between a first source position, in which the X-rays are directed from the radiation source toward the surface of the sample at a grazing angle, and a second source position, in which the X-rays are directed from the radiation source toward the surface of the sample in a vicinity of a Bragg angle of the sample.

3. The apparatus according to claim 1, wherein the first and second mirrors are offset in azimuth and are configured to receive and focus the X-rays simultaneously.

4. The apparatus according to claim 3, wherein the radiation source comprises a beam block, which is movable to block a part of the X-rays emitted from the X-ray tube so that only one of the converging and collimated beams strikes the sample.

5. The apparatus according to claim 1, wherein the first and second mirrors comprise doubly-curved structures.

6. The apparatus according to claim 2, wherein the motion assembly is operative to move the detector assembly between a first detector elevation, at which the detector assembly senses the X-rays scattered from the sample at the grazing angle, and a second detector elevation, at which the detector assembly senses the X-rays scattered from the surface in the vicinity of the Bragg angle.

7. The apparatus according to claim 6, wherein the motion assembly is operative to move the detector assembly at the first detector elevation between a first azimuth, at which the detector assembly senses small-angle scattering of the X-rays, and a second, higher azimuth, at which the detector assembly senses the X-rays that are diffracted from an in-plane structure on the surface of the sample.

8. The apparatus according to claim 1, wherein the detector assembly comprises a detector array having a first detector configuration for resolving the scattered X-rays along a first axis perpendicular to the surface of the sample, and a second detector configuration for resolving the scattered X-rays along a second axis parallel to the surface.

9. The apparatus according to claim 8, wherein the signal processor is adapted to process the output signals from the detector assembly in the first detector configuration so as to determine a reflectance of the surface as a function of elevation angle relative to the surface, and to process the output signals from the detector assembly in the second detector configuration so as to determine a scattering profile of the surface as a function of azimuthal angle in a plane of the surface.

10. The apparatus according to claim 2, wherein the signal processor is adapted to process the output signals from the detector assembly while the radiation source emits the first beam and is in the first source position so as to acquire an X-ray reflectance (XRR) spectrum of the surface, and to process the output signals from the detector assembly while the radiation source emits the second beam and is in the first source position so as to acquire at least one of a small-angle X-ray scattering (SAXS) spectrum and a grazing-incidence X-ray diffraction (XRD) spectrum of the surface, and to process the output signals from the detector assembly while the radiation source is in the second source position so as to acquire a high-angle XRD spectrum of the surface.

11. The apparatus according to claim 10, wherein the signal processor is adapted to acquire a high-resolution XRD spectrum while the radiation source is in the second source position and emits the first beam and to acquire a low-resolution XRD spectrum while the radiation source is in the second source position and emits the second beam.

12. The apparatus according to claim 11, wherein the motion sensor is adapted to position the detector assembly at a first distance from the surface of the sample for acquisition of the high-resolution XRD spectrum and to position the detector assembly at a second distance from the surface, smaller than the first distance, for acquisition of the low-resolution XRD spectrum.

13. The apparatus according to claim 10, wherein the sample comprises at least one surface layer, and wherein the signal processor is arranged to analyze two or more of the XRR, SAXS and XRD spectra together in order to determine a property of the at least one surface layer.

14. The apparatus according to claim 13, wherein the property comprises at least one of a thickness, a density, a surface quality, a porosity, and a crystalline structure.

15. The apparatus according to claim 1, and comprising a knife edge, which is arranged parallel to the surface of the sample and adjacent to the selected area so as to define a gap between the surface and the knife edge and to block a portion of the beam that does not pass through the gap.

16. The apparatus according to claim 15, and comprising a beam block, which is arranged to block the X-rays that have passed through the gap and continued to propagate along the beam axis, without blocking the scattered X-rays in an angular range of interest.

17. The apparatus according to claim 15, wherein the knife edge comprises a cylinder of X-ray absorbing material.

18. The apparatus according to claim 1, and comprising a mounting assembly, for receiving and adjusting an orientation of the sample during the analysis, wherein the radiation source is adapted to direct the X-ray beam toward a selected area on the surface of the sample, and wherein the signal processor is adapted to receive a tilt map indicating a characteristic tilt angle of the surface, and to determine a tilt angle of the selected area based on the tilt map, and to direct the mounting assembly to adjust the orientation of the sample so as to compensate for the estimated tilt angle.

19. A method of analyzing a sample, comprising:
operating a radiation source so as to direct a first, converging beam of X-rays toward a surface of the sample and to direct a second, collimated beam of the X-rays toward the surface of the sample, by positioning a first mirror to focus the X-rays from an X-ray source into the converging beam and positioning a second mirror to focus the X-rays from the X-ray source into the collimated beam; and sensing the X-rays scattered from the sample as a function of angle responsively to either of the converging beam and the collimated beam so as to determine a characteristic of the sample.

20. The method according to claim 19, wherein operating the radiation source comprises moving the radiation source between a first source position, in which the X-rays are directed from the radiation source toward the surface of the sample at a grazing angle, and a second source position, in which the X-rays are directed from the radiation source toward the surface of the sample in a vicinity of a Bragg angle of the sample.

21. The method according to claim 19, wherein the first and second mirrors are offset in azimuth and are configured to receive and focus the X-rays simultaneously.

22. The method according to claim 21, wherein operating the radiation source comprises moving a beam block to block a part of the X-rays emitted from the X-ray tube so that only one of the converging and collimated beams strikes the sample.

23. The method according to claim 19, wherein the first and second mirrors comprise doubly-curved structures.

24. The method according to claim 20, wherein sensing the X-rays comprises capturing the scattered X-rays using a detector, and moving the detector between a first detector elevation, at which the detector senses the X-rays scattered from the sample at the grazing angle while the radiation source is in the first source position, and a second detector elevation, at which the detector senses the X-rays scattered from the surface in the vicinity of the Bragg angle while the radiation source is in the second source position.

25. The method according to claim 24, wherein moving the detector further comprises moving the detector at the first detector elevation between a first azimuth, at which the detector assembly senses small-angle scattering of the X-rays, and a second, higher azimuth, at which the detector assembly senses the X-rays that are diffracted from an in-plane structure on the surface of the sample.

26. The method according to claim 19, wherein sensing the X-rays comprises deploying a detector array in a first detector configuration for resolving the scattered X-rays along a first axis perpendicular to the surface of the sample, and a second detector configuration for resolving the scattered X-rays along a second axis parallel to the surface.

27. The method according to claim 26, wherein sensing the X-rays comprises processing an output of the detector array in the first detector configuration in order to determine a reflectance of the surface as a function of elevation angle relative to the surface, and processing the output of the detector array in the second detector configuration in order to determine a scattering profile of the surface as a function of azimuthal angle in a plane of the surface.

28. The method according to claim 20, wherein sensing the X-rays comprises acquiring an X-ray reflectance (XRR) spectrum of the surface while the radiation source is in the first source position and directs the first beam toward the surface, acquiring at least one of a small-angle X-ray scattering (SAXS) spectrum and a grazing-incidence X-ray diffraction (XRD) spectrum of the surface while the radiation source is in the first source position and directs the second beam toward the surface, and acquiring a high-angle XRD spectrum of the surface while the radiation source is in the second source position.

29. The method according to claim 28, wherein acquiring the XRD spectrum comprises acquiring a high-resolution XRD spectrum while the radiation source is in the second source position and directs the first beam toward the surface and acquiring a low-resolution XRD spectrum while the radiation source is in the second source position and directs the second beam toward the surface.

30. The method according to claim 29, wherein sensing the X-rays comprises positioning a detector to receive the scattered X-rays at a first distance from the surface of the sample for acquisition of the high-resolution XRD spectrum and positioning the detector to receive the scattered X-rays at a second distance from the surface, smaller than the first distance, for acquisition of the low-resolution XRD spectrum.

31. The method according to claim 28, wherein the sample comprises at least one surface layer, and comprising analyzing two or more of the XRR, SAXS and XRD spectra together in order to determine a property of the at least one surface layer.

32. The method according to claim 31, wherein the property comprises at least one of a thickness, a density, a surface quality, a porosity, and a crystalline structure.

33. The method according to claim 19, and comprising positioning a knife edge parallel to the surface of the sample and adjacent to the selected area so as to define a gap between the surface and the knife edge and to block a portion of the beam that does not pass through the gap.

34. The method according to claim 33, and comprising positioning a beam block to block the X-rays that have passed through the gap and continued to propagate along the beam axis, without blocking the scattered X-rays in an angular range of interest.

35. The method according to claim 33, wherein the knife edge comprises a cylinder of X-ray absorbing material.

36. The method according to claim 19, wherein operating the radiation source comprises directing the X-ray beam toward a selected area on the surface of the sample, and comprising:
   providing a tilt map indicating a characteristic tilt angle of the surface;
   determining a tilt angle of the selected area based on the tilt map; and
   adjusting an orientation of the sample to compensate for the estimated tilt angle.

* * * * *

UNITED STATES PATENT AND TRADEMARK OFFICE
CERTIFICATE OF CORRECTION

PATENT NO. : 7,551,719 B2
APPLICATION NO. : 11/200857
DATED : June 23, 2009
INVENTOR(S) : Boris Yokhin et al.

It is certified that error appears in the above-identified patent and that said Letters Patent is hereby corrected as shown below:

Title Page;
   Front page, (73) Assignee: "Jordan Valley Semiconductord Ltd" should read --Jordan Valley Semiconductors Ltd--; and Front page, (74) Attorney, Agent, or Firm, "Weingarte," should read --Weingarten,--.

Signed and Sealed this

Eighteenth Day of May, 2010

David J. Kappos
*Director of the United States Patent and Trademark Office*